United States Patent [19]

Weber et al.

[11] Patent Number: 5,434,275

[45] Date of Patent: Jul. 18, 1995

[54] DIBENZOFURANYLBIPHENYLS

[75] Inventors: Kurt Weber, Basel, Switzerland; Claude Eckhardt, Riedisheim, France; Hans R. Meyer, Binningen, Switzerland

[73] Assignee: Ciba-Geigy Corporation, Ardsley, N.Y.

[21] Appl. No.: 221,733

[22] Filed: Apr. 1, 1994

Related U.S. Application Data

[60] Division of Ser. No. 55,643, Apr. 30, 1993, Pat. No. 5,326,491, which is a continuation-in-part of Ser. No. 827,523, Jan. 28, 1992, abandoned, which is a continuation of Ser. No. 514,446, Apr. 25, 1990, abandoned.

[30] Foreign Application Priority Data

Apr. 28, 1989 [CH] Switzerland .................. 1629/89

[51] Int. Cl.$^6$ .................. C07D 307/80; C07D 307/82
[52] U.S. Cl. .................................................. 549/469
[58] Field of Search ........................................ 549/469

[56] References Cited

U.S. PATENT DOCUMENTS

| 3,741,903 | 6/1973 | Evans | 252/195 |
|---|---|---|---|
| 3,859,350 | 1/1975 | Sahm | 106/176 |
| 3,864,333 | 2/1975 | Sahm | 260/240 |
| 3,892,807 | 7/1975 | Sahm | 260/566 |
| 3,994,879 | 11/1976 | Sahm | 260/240 |
| 4,002,423 | 1/1977 | Sahm | 8/1 |
| 4,052,433 | 10/1977 | Sahm | 260/465 |
| 4,122,256 | 10/1978 | Sahm | 542/423 |
| 4,578,206 | 3/1986 | Walker | 252/95 |
| 4,579,678 | 4/1986 | Walker | 252/95 |
| 4,670,882 | 6/1987 | Telle | 372/53 |
| 4,865,759 | 9/1989 | Coyne | 252/186 |
| 4,929,377 | 5/1990 | Emmons | 251/100 |
| 5,089,166 | 2/1992 | Clements | 252/186 |

FOREIGN PATENT DOCUMENTS 0145438 6/1985 European Pat. Off. .
2756583 6/1979 Germany .

*Primary Examiner*—Bernard Dentz
*Attorney, Agent, or Firm*—Kevin T. Mansfield

[57] ABSTRACT

Novel dibenzofuranylbiphenyl compounds of the formula (I)

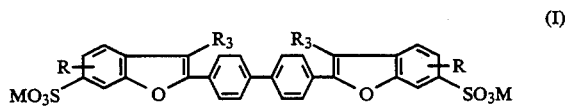

which are unsubstituted or are monosubstituted or polysubstituted by radicals R=hydrogen, $C_1$–$C_4$alkyl, $C_1$–$C_4$alkoxy, halogen, phenoxy and benzyloxy and in which $R_3$ is $C_1$–$C_4$alkyl, halogen or phenyl and M is hydrogen and/or one equivalent of a non-chromophoric cation and the preparation and use thereof for fluorescent whitening are described.

8 Claims, No Drawings

DIBENZOFURANYLBIPHENYLS

This is a division of Ser. No. 08/055,643, filed Apr. 30, 1993, now U.S. Pat. No. 5,326,491, which is a continuation-in-part of Ser. No. 07/827,523, filed Jan. 28, 1992, now abandoned, which is a continuation of Ser. No. 07/514,446, filed Apr. 25, 1990, now abandoned.

The present invention relates to dibenzofuranylbiphenyl compounds which are selectively sulfonated, to their preparation and to their use as fluorescent whitening agents for the fluorescent whitening of textile materials or paper or to their use in detergents containing a peracid.

Mixtures of sulfonated benzofuranylbiphenyl compounds of undefined composition and structure and their use as fluorescent whitening agents have been known for a long time (DE-A 22 38 734, DE-A 22 38 628, DE-A 23 61 338 and DE-A 28 43 850). However, it has hitherto not been possible to prepare individual compounds of these mixtures having uniform structures.

It has now been found, surprisingly, that sulfonated dibenzofuranylbiphenyl compounds having a definite structure can be prepared selectively by specific processes.

The invention therefore relates to novel dibenzofuranylbiphenyl compounds of the formula (I)

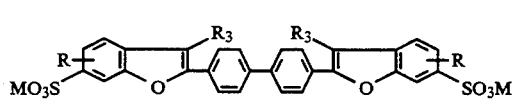

which are unsubstituted or are monosubstituted or polysubstituted by radicals R=hydrogen, $C_1$-$C_4$alkyl, $C_1$-$C_4$alkoxy, halogen, phenoxy and benzyloxy and in which is $C_1$-$C_4$alkyl, halogen or phenyl and M is hydrogen and/or one equivalent of a non-chromophoric cation.

Suitable halogens are, in particular, fluorine, chlorine and bromine, but especially chlorine.

Suitable $C_1$-$C_4$alkyl radicals (or $C_1$-$C_4$alkoxy radicals) are unbranched or branched alkyl (or alkoxy, respectively) radicals. These alkyl (or alkoxy, respectively) radicals can in turn be substituted by, for example, aryl (phenyl or tolyl), $C_1$-$C_4$alkyl, $C_1$-$C_4$alkoxy, OH or CN groups. On the other hand, the phenyl radicals can be substituted by alkyl, alkoxy or halogen.

When M is a non-chromophoric cation, it is, for example, an alkaline earth metal, such as magnesium and calcium, but is preferably an alkali metal, such as lithium, sodium or potassium, and substituted or unsubstituted ammonium, such as ammonium, mono-, di- or tri-ethanolammonium, mono-, di- or tri-propanolammonium or mono-, di-, tri- or tetra-methylammonium.

Compounds of the formula (II)

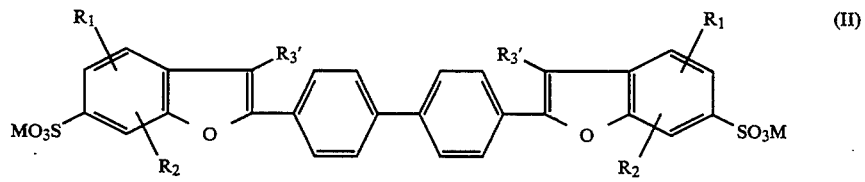

in which $R_1$ is hydrogen, $C_1$-$C_4$alkyl, chlorine or $C_1$-$C_4$alkoxy, $R_2$ is hydrogen, $C_1$-$C_4$alkyl, chlorine or $C_1$-$C_4$alkoxy, $R_3'$ is $C_1$-$C_4$alkyl, chlorine or phenyl, and M is hydrogen and/or one equivalent of a non-chromophoric cation are preferred.

Compounds of the formula (III)

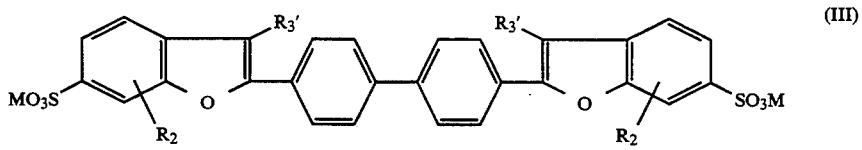

in which $R_2$, $R_3'$ and M are as defined above are, however, of particular interest. $R_2$ is preferably hydrogen, 5-methyl, 5-ethyl or 5-chlorine and $R_3'$ is preferably methyl, ethyl or phenyl.

This invention also relates to processes for the preparation of the compounds of the formula (I) which comprise reacting one mole of the compound of the formula (X)

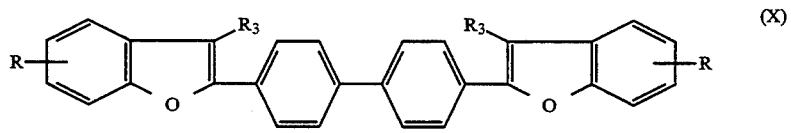

which is unsubstituted or is monosubstituted or polysubstituted by radicals R=hydrogen, $C_1$-$C_4$alkyl, $C_1$-$C_4$alkoxy, halogen, phenoxy and benzyloxy and in which $R_3$ is $C_1$-$C_4$ alkyl, halogen or phenyl, with a) at least stoichiometric mounts of an $SO_3$/base complex, in an inert organic solvent, at temperatures from 20° C. up to the boiling point of the solvent used, or b) treating the compound of the formula (X) with chlorosulfonic acid at 0°–80° C. or c) treating the compound of the formula (X) with glacial acetic acid and concentrated sulfuric acid or oleum at temperatures from 80° to 140° C.

and neutralizing the resulting sulfonic acids, if appropriate, with suitable bases, such as aqueous alkali, ammonia or amines. Sulfochlorides which may be formed as a by-product are saponified previously or at the same time with water at elevated temperatures.

The compounds of the formula (X) are in part known and can be prepared by a known method.

The novel starting compounds of the formula (X) in which $R_3$ is Cl are obtained by chlorinating compounds of the formula (X) in which $R_3$ is H by means of phosphorus pentachloride at 100° to 200° in suitable solvents, such as chlorobenzene or dichlorobenzene.

$SO_3$/base complexes are to be understood as meaning addition compounds of $SO_3$ with organic bases, for example dioxane, preferably nitrogen-containing bases, for example triethylamine, N-ethyldiisopropylamine, dimethylformamide (DMF) and pyridine. The stability of these addition compounds is decisive for the degree of sulfonation. Thus 2 to 6, in particular 3 to 5, moles of $SO_3$/pyridine complex (relative to the $SO_3$ content) are used per mole of the compound of the formula (X), or 2 to 6, in particular 3 to 5, moles of $SO_3$/DMF complex (relative to the $SO_3$ content) are used per mole of the compound of the formula (X). $SO_3$/base complexes are known and can be prepared by known methods (E. E. Gilbert, E. P. Jones, Ind. Enging. Chem. 49, No. 9, Part II, pages 1553 et seq (1957); Beilstein 20, III/IV, 2232).

In process b) especially one mole of the compound of the formula (X) is reacted with 2 to 20, in particular 2 to 4, moles of chlorosulfonic acid at temperatures from 0° C. to 80° C., in particular 5° C. to 40° C., in the absence, or preferably in the presence, of an inert organic solvent.

Examples of inert organic solvents are saturated aliphatic hydrocarbons, such as gasoline, petroleum ether and ligroin, halogenated aliphatic hydrocarbons, such as chloroform, carbon tetrachloride, dichloroethane, trichloroethane, tetrachloroethane, dichloropropane, trichloropropane, dichlorodifluoromethane and dichlorotetrafluoroethane, chlorobenzenes, such as mono-, di- and tri-chlorobenzene, nitrobenzenes, such as nitrobenzene and nitrotoluene, and monocyclic or dicyclic hydrocarbons, such as cyclohexane, methylcyclohexane and decalin.

Compounds of the formula (I) are used for the fluorescent whitening of textile materials, in which connection polyamides, wool and cotton should be singled out particularly, and of paper.

Based on the increased proportion of synthetic fibres or mixed fibres in the textiles produced nowadays, and the desire to give up washing coloured laundry separately, as well as from measures for saving energy, laundry is no longer washed at 90° C.–95° C. or at the boil in many countries, but at lower temperatures. This had the result that the perborates hitherto mostly contained in detergents and acting as bleaching agents have had to be activated by assistants, for example tetraacetylethylenediamine (TAED), in order to obtain acceptable bleaching effects even at washing temperatures of 60°–80° C. At even lower washing temperatures the perborate/activator systems no longer give satisfactory results either.

For some time, therefore, detergents containing stronger bleaching agents, for example peracids, are described (German Offenlegungsschrift 27 56 583, EP-A 145 438, GB 2 141 754, GB 2 141 755, US 4,028,263 and GB 59 272). On the one hand these novel bleaching agents admittedly display excellent bleaching effects even at temperatures down to 20° C., but, on the other hand, they destroy the customary fluorescent whitening agents present in detergents.

The special dibenzofuranyl compounds described above exhibit an excellent stability in detergents containing such strong bleaching agents. Under avenge conditions of storage and even under more rigorous conditions (temperatures of over 30° C. and over 60% humidity), these special dibenzofuranyl fluorescent whitening agents are completely stable in the detergent for several months or, at the most, are degraded to an extent which does not interfere in practice.

The invention also relates, therefore, to detergents which are stable on storage and contain 0.5 to 30% of an inorganic or organic peracid or salts thereof or mixtures of peracids or salts thereof and also 0.03% to 0.8% of a fluorescent whitening agent or a mixture of fluorescent whitening agents, in which the fluorescent whitening agents are dibenzofuranylbiphenyl compounds of the formula (I)

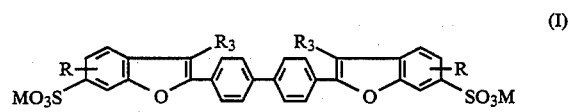

(I)

which are unsubstituted or are monosubstituted or polysubstituted by radicals R=hydrogen, $C_1$–$C_4$alkyl, $C_1$–$C_4$alkoxy, halogen, phenoxy and benzyloxy and in which $R_3$ is $C_1$–$C_4$alkyl, halogen or phenyl and M is hydrogen and/or one equivalent of a non-chromophoric cation.

Compounds of the formula (II)

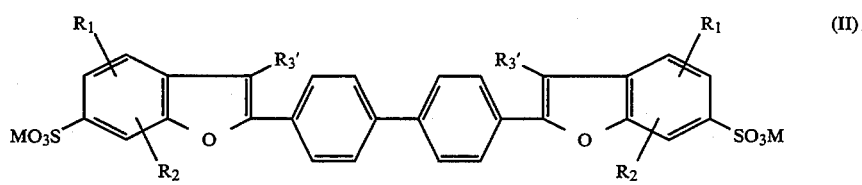

(II)

in which $R_1$ is hydrogen, $C_1$–$C_4$alkyl, chlorine or $C_1$–$C_4$alkoxy, $R_2$ is hydrogen, $C_1$–$C_4$alkyl, chlorine or $C_1$–$C_4$alkoxy, $R_3'$ is $C_1$–$C_4$alkyl, chlorine or phenyl and M is hydrogen and/or one equivalent of a non-chromophoric cation, are preferred.

Compounds of the formula (III)

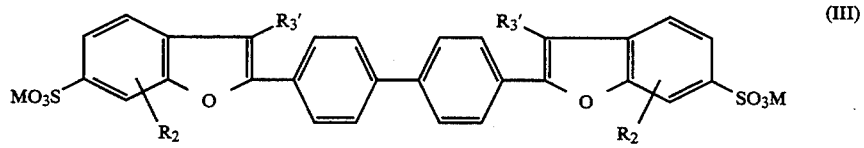

(III)

in which $R_2$, $R_3'$ and M are as defined above are, however, of particular interest. $R_2$ is preferably hydrogen, 5-methyl, 5-ethyl or 5-chlorine and $R_3'$ is preferably methyl, ethyl or phenyl.

The peracids or salts thereof are the organic or inorganic compounds described in the literature or available on the market which bleach textiles at temperatures as low as 20° C. In particular, the organic peracids are, for example, monoperacids or polyperacids having alkyl chains of at least 3, preferably 6 to 20, carbon atoms, but particularly diperoxydicarboxylic acids having 6 to 12 C atoms, such as diperoxyperazelaic acid, diperoxypersebacic acid, diperoxyphthalic acid and/or diperoxydodecanedioic acid (DPDDA) are of interest. It is also possible, however, to employ very active inorganic peracids, such as persulfate and/or percarbonate. The amount of organic peracids to be employed is preferably 0.5% to 10%, in particular 1% to 5%, and of inorganic peracids preferably 1% to 30%, in particular 10% to 20%, relative to the total weight of detergent and, if appropriate, in combination with small amounts of compounds which enhance the bleaching action of the peracids, such as divalent metal salts having a catalytic action, such as are described in U.S. Pat. No. 4,655,782 and U.S. Pat. No. 4,655,953. It is preferable to use metal salts of copper and/or manganese.

It is, of course, also possible to employ mixtures of organic and/or inorganic peracids and/or persalts.

The addition of the peracids to the detergent is effected, in particular, by mixing the components, for example by means of screw-metering systems and/or fluidized bed mixers.

The detergents are dry detergents of customary compositions. As a rule, in addition to the combination according to the invention of peracid and fluorescent whitening agent, they contain, for example, anionic, nonionic, amphoteric and/or cationic surfactants, builders, for example pentasodium tripolyphosphate, or substitute products, such as phosphonates, polycarboxylates, acrylic/maleic copolymers, zeolites, nitrilotriacetate or ethylenediaminotetraacetic acid, soil suspending agents, for example sodium carboxymethylcellulose, salts for adjusting the pH, for example alkali or alkaline earth metal silicates, foam regulators, for example soap, salts for adjusting the spray drying and granulating properties, for example sodium sulfate, perfumes, and also, if appropriate, antistatic and softening agents, enzymes, photobleaching agents, pigments and/or shading agents. These constituents should, of course, be stable to the bleaching system employed.

Thanks to the combination according to the invention it is possible to provide detergents which meet the conventional standard, for example with regard to detergent power, stain removal and reviving the appearance of the washed articles, even when washing is carried out at temperatures from 20° C. to 60° C. Coloured laundry and white laundry can advantageously thus be washed together, independently of the fibre.

The following examples serve to illustrate the invention; parts and percentages are by weight.

EXAMPLE 1

6.5 ml of 65% oleum in 200 ml of glacial acetic acid are initially introduced.

13.7 g of the compound of the formula

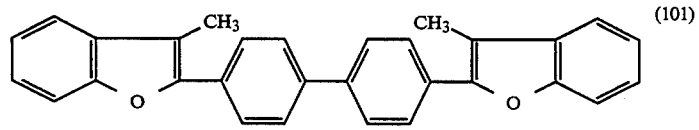

(101)

are then added with stirring, and the mixture is heated to 100°–105° C. and stirred at this temperature for 1 hour. After cooling to 60° C. 25 g of sodium acetate in 40 ml of water are added, the mixture is allowed to cool to room temperature and the product which has crystallized out is filtered off with suction. After recrystallization from a mixture of 800 ml of water and 400 ml of methylcellosolve and a second recrystallization from a mixture of 500 ml of water and 500 ml of methylcellosolve, 12 g of the compound of the formula

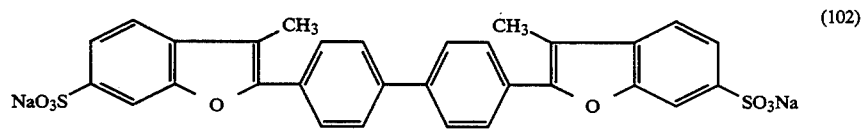

(102)

are obtained in the form of a pale yellow crystalline powder. UV absorption: $\lambda max = 351$ nm; $\epsilon = 74{,}450$ (in 1:1 DMF/$H_2O$).

The compound of the formula

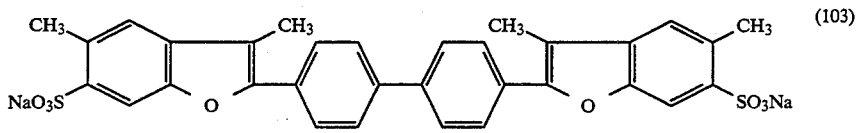

is obtained analogously as a pale yellow crystalline powder. UV absorption spectrum: $\lambda_{max}$:353 nm; $\epsilon=76,300$ (in 1:1 DMF/H$_2$).

The compound of the formula (101) can be obtained as specified in DE-A 22 38 628.

EXAMPLE 2

62.1 g of the compound of the formula (101) and 50 g of sulfurtrioxide/dimethylformamide complex are initially introduced with stirring in 370 ml of nitrobenzene, and the mixture is heated to 115° C. and stirred for 2 hours at this temperature. After cooling to 60° C. the pH is adjusted to 9 with 10% sodium hydroxide solution, the nitrobenzene is removed by steam distillation and the aqueous suspension is cooled to 10° C., the product is filtered off with suction and washed with 5% sodium chloride solution and dried in vacuo at 100° C. This gives 86.3 g of a pale yellow product containing 94.6% of the compound (102).

EXAMPLE 3

18.5 ml of 65% oleum are initially introduced into 450 ml of glacial acetic acid. 44.2 g of the compound of the formula

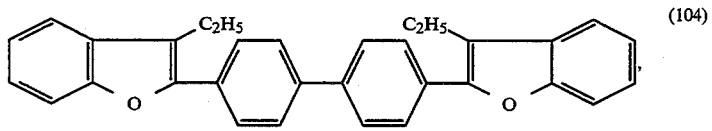

melting point: 190°–191° C., are then introduced, with stirring, and the mixture is heated to 100° C. and stirred for 1 hour at this temperature.

After cooling to room temperature the reaction mixture is poured into a solution of 100 g of sodium acetate in 450 ml of water, and the mixture is heated to 100° C., 7 g of active charcoal are added and the mixture is filtered while hot. After cooling to room temperature the product which has crystallized out is filtered off with suction and dried in vacuo. The product thus obtained is recrystallized twice from a mixture of 150 ml of ethanol and 150 ml of water, with the addition of active charcoal. This gives 45 g of the compound of the formula

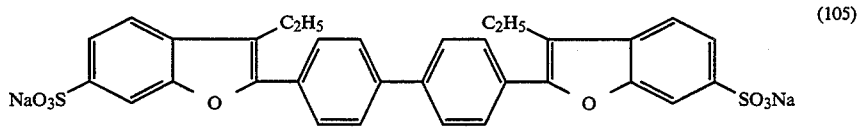

as a pale yellow crystalline powder, UV absorption spectrum: $\lambda_{max}$:350 nm; $\epsilon=69,864$ (1:1 DMF/H$_2$O).

The compound of the formula (104) can be obtained analogously to the compound of the formula (101).

EXAMPLE 4

19.4 g of the compound of the formula

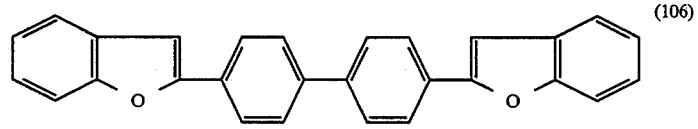

and 25.0 g of phosphorus pentachloride are stirred in 150 ml of chlorobenzene, and the suspension is heated to reflux temperature. When the starting material has dissolved completely and the evolution of hydrochloric acid gas is complete (approx. 1 hour), the mixture is allowed to cool and 50 ml of methanol are added cautiously. The precipitated product is filtered off with suction, washed with methanol and dried in vacuo. This gives 19.6 g of the compound of the formula

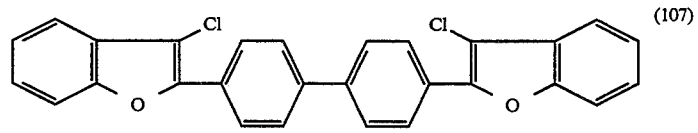

in the form of nearly colourless crystals. Melting point 210°–11° (recrystallized from xylene).

The compound of the formula

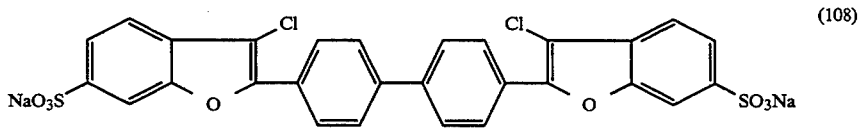

(108)

is obtained by sulfonation with chlorosulfonic acid in tetrachloroethane in accordance with Example 6.

EXAMPLE 5

A solution of 1.4 ml of chlorosulfonic acid in 20 ml of tetrachloroethane is added dropwise in the course of ¼ hour, with stirring and at 90° C., to a suspension of 4.6 g of the compound of the formula (107) and 4.8 g of thionyl chloride in 30 ml of tetrachloroethane. When the reaction is complete (90°–120° C.), the mixture is allowed to cool and the precipitated product is filtered off with suction and dried in vacuo at 90° C. This gives 5.3 g of the disulfochloride [melting point 297° (decomposition) recrystallized from chlorobenzene]. 3.3 g of disulfochloride in 18 ml of pyridine and 2 ml of water are heated at reflux temperature for 20 minutes. The solution is evaporated to dryness in vacuo and the residue is recrystallized from 7:3 to 9:1 n-propanol/water, using active charcoal for clarification by filtration. This gives 2.4 g of the compound of the formula reached. The mixture is evaporated to dryness in vacuo on a rotary evaporator, the residue is dissolved in a mixture of 3:2 n-propanol/water, n-propanol is added until a ratio of 2:1 is reached, the mixture is filtered while hot with active charcoal, and the filtrate is concentrated while adding further n-propanol until the product crystallizes out. This product is filtered off with suction at 0° C., washed with n-propanol and dried in vacuo. This gives 8.8 g of the compound of the formula

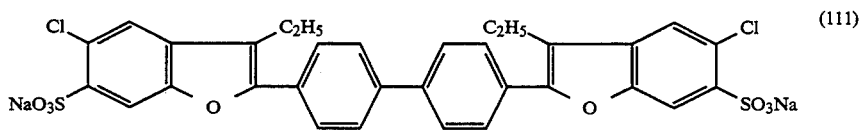

(111)

which still contains 1 mole of water of crystallization.

The compound of the formula (110) used as the starting material is prepared as follows: 36 g of 30% sodium methylate solution are added dropwise, with stirring and at room temperature, to a solution of 36.9 g of 5-chloro-2-hydroxypropiophenone in 100 ml of DMF. After 2 hours 26 g of 4,4'-bischloromethylbiphenyl are added and the mixture is heated for 3 hours at 100°, in the course of which methanol may distill off. The mixture is cooled to 5° C. and the precipitated product is

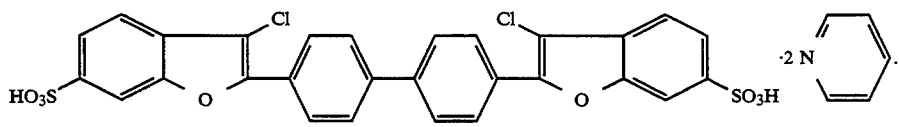

(109)

EXAMPLE 6

5.24 g of chlorosulfonic acid are added dropwise in the course of ½ hour, with stirring and at 5° C., to a fine dispersion of 7.7 g of the compound of the formula filtered off with suction, washed with ethanol and water and dried in vacuo at 100° C. This gives 47.6 g of the compound of the formula

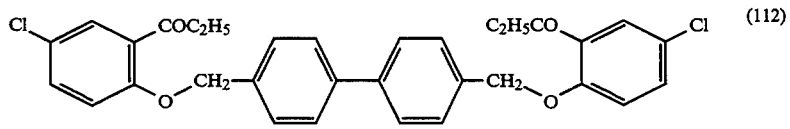

(112)

melting point 167°–8° (toluene).

2.7 g of sodium methylate are added in portions in the

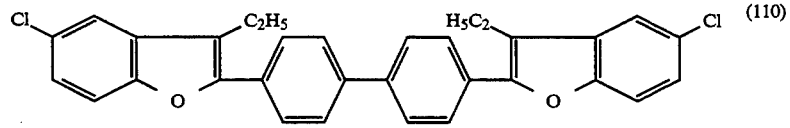

(110)

in 100 ml of tetrachloroethane. Stirring is continued for a further 2 hours at room temperature, and the dark product is filtered off with suction, washed with tetrachloroethane and suspended in 150 ml of water. The residual tetrachloroethane is removed by azeotropic distillation with water at elevated temperature and, at the same time, the mixture is neutralized with 30% sodium hydroxide solution until a constant pH of 9 is course of ½ hour at 130° C. to a solution of 27.4 g of the compound of the formula (112) in 70 ml of dimethyl sulfoxide. After 2 hours the mixture is allowed to cool to room temperature and is diluted with 60 ml of methanol, and the precipitated product is filtered off with suction, washed with methanol and water and dried in vacuo at 100°. This gives 22.8 g of the compound of the formula (110); melting point 233°–5° C. (xylene).

EXAMPLE 7

The following bisphenol ethers (A₁), dibenzofuranes (A₂) and dibenzofuranedisulfonic acids (A₃) are prepared from the corresponding components in the manner described above:

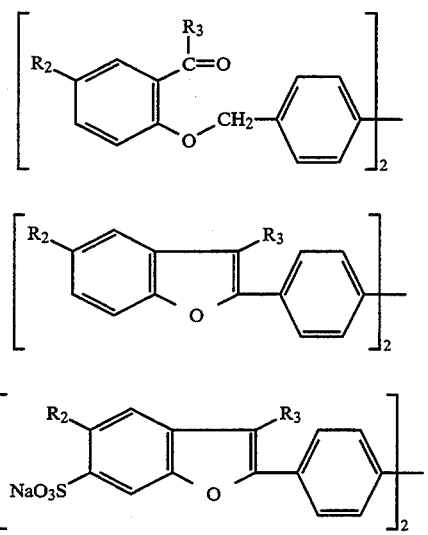

| $R_2$ | $R_3$ | ($A_1$) m.p. (°C.) | ($A_2$) m.p. (°C.) | ($A_3$) m.p. (°C.) | No. |
|---|---|---|---|---|---|
| Cl | $CH_3$ | 159–60 | 232–4 | >300 | (113) |
| $CH_3$ | $C_2H_5$ | 166–68 | 214–5 | >300 | (114) |
| $OCH_3$ | $CH_3$ | 145–46 | 240–2 | >300 | (115)[1] |
| H | $C_6H_5$ | 170–71 | 264–6 | >300 | (116)[2] |
| $CH_3$ | $C_6H_5$ | 208–10 | 256–7 | >300 | (117)[2] |

[1] In order to obtain the more soluble ammonium salt, neutralization is carried out with ammonia instead of sodium hydroxide solution, after the mixture has been boiled and the residual tetrachloroethane disrifled off.
[2] Sulfonation with SO₃-dimethylformamide complex (20% excess) in nitrobenzene at 120° C. overnight.

EXAMPLE 8

A piece of polyamide 66 (nylon warpknit fabric) is heated from 40° C. to 98° C. in the course of 30 minutes at a liquor ratio of 1:20 in soft water containing 0.1% of the compound of the formula (102) (percent by weight relative to the textile material) and 3 g/l of stabilized bisulfite and 1 ml/l of 80% acetic acid, then subjected to treatment at 98° C. for 30 minutes, cooled again to 40° C. in the course of 15 minutes, given a cold rinse and dried in a drying cabinet at 60° C.

A high, brilliant degree of whiteness results. When exposed to light in a ®Xenotest apparatus by the customary standard method, this white effect displays a very good fastness to light.

EXAMPLE 9

The procedure followed is analogous to that in Example 8, but the compound (103) or the compound (108) or the compound (116) is used instead of the compound (102).

High, brilliant white effects having very good to excellent fastness to light also result in this case.

EXAMPLE 10

Detergent granules having a residual moisture content of approx. 5% are prepared by spray drying a slurry consisting of 1 part of water and 1 part of a detergent of the following composition:

8.4 g of linear dodecylbenzenesulfonate,
3.1 g of tallow alcohol tetradecaneethylene glycol ether (14 EO),
3.7 g of Na soap (mainly composed of behenic acid and $C_{14}$-$C_{20}$-acids),
45.8 g of Na tripolyphosphate,
7.9 g of Na silicate,
2.0 g of Mg silicate,
1.2 g of carboxymethylcellulose,
0.2 g of ethylenediaminetetraacetate,
22.2 g of Na sulfate and
0.1 g of the compound (102)

4 g of this detergent are dissolved in 1 l of water (12° of German hardness) at a temperature of 30° C. Five pieces of bleached cotton, each 10 g, are washed for 15 minutes at 30° C. in this bath, then rinsed under cold running water and spun for 30 seconds in a spin-dryer at a speed of approx. 1,000 revolutions/minute. This washing process is carried out three times and the pieces of cotton are then dried and their degree of whiteness is determined by the Ganz method using a colorimeter (Zeiss RFC 3). A high degree of whiteness of over 175 is obtained. The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No.5 (1972).

EXAMPLE 11

The procedure followed is analogous to that in Example 10, but the compound (103) is used instead of the compound (102). A high white effect is obtained after washing three times.

If washing is carried out at 60° C. or 90° C. instead of at 30° C. under otherwise identical conditions, the resulting white effects are even higher.

EXAMPLE 12

A washing powder is prepared as described under Example 10.3 g of diperoxydodecanedioic acid (DPDDA) are then homogeneously admixed to 100 g of these granules in the dry state.

Storage test. Samples of the detergent W thus obtained (granules A+peracid B) are treated as follows:
firstly, to monitor the initial value, the content of FWA (fluorescent whitening agent) is determined immediately by extraction and spectrophotometric measurement of extinction (theoretical value: 0.1% of FWA relative to the weight of the granules A);
secondly, the granules are stored for definite periods of time in cardboard packets as used for commercial washing powders, i.e. with a coating, and under selected and monitored conditions of temperature and humidity. The FWA content of each detergent is determined immediately after storage. The difference from the initial value, expressed as a percentage, is a measure of the stability of the FWA to the appropriate bleaching agent in the washing powder.

The determination of FWA mentioned above is carried out as follows: the washing powder is thoroughly homogenized by grinding and 200 ml of solvent, consisting of 9 parts of dimethyl sulfoxide and 1 part of water, are added to 1 g of the washing powder, and the mixture is stirred for 30 minutes at room temperature. It is then centrifuged for 30 minutes. A sample of the clear solution thus obtained is transferred by means of a pipette into a 1 cm quartz cell and its extinction in the UV range is determined at the absorption maximum against a standard solution of the FWA concerned. The extinction is proportional to the concentration of FWA.

The packet is stored in the opened state at a temperature of 30° C. and a relative humidity of 80–85% for 8 weeks, as can occur in household use, for example in a washroom. Quantitative determination of the FWA shows that the fluorescent whitening agent has excellent stability.

EXAMPLE 13

Detergents are prepared as in Example 12. The packets are stored under identical conditions, but in the closed state and for 6 months, as can occur in practice between the production of the detergent and its use in the home. Here too the compound (102) displays a very good stability.

EXAMPLE 14

A detergent is prepared as described under Example 10. 100 g of these granules are then homogeneously mixed in the dry state with 14 g of K monopersulfate and 0.4 mg of $CuSO_4$ (anhydrous).

After 3 months storage in a closed packet at room temperature (20°–25° C.) only a very small proportion of the compound (102), not detectable in the practical use of the detergent, has been destroyed.

EXAMPLE 15

Detergents are prepared and treated as under Example 10, but 0.1 g of the compounds (103) or (108) or (113) is employed in each case instead of the compound (102).

The storage tests are carried out as described in Examples 12 and 13. Here too the compounds (103), (108) and (113) display an excellent stability.

EXAMPLE 16

Detergents are prepared and treated as described in Example 14, but the compound (102) is replaced in each case by 0.1 g of the compounds (103) or (108) or (113). Under these conditions too the compounds display a very good stability.

EXAMPLE 17

The following washing composition is prepared:

7.8% sodium alkanebenzenesulfonate
2.8% tallow alcohol tetradecanethylene glycol ether (14EO)
3.4% sodium soap
42.5% sodium triphosphate
7.3% sodium silicate
1.85% magnesium silicate
1.15% carboxymethylcellulose
0.2% ethylenediamine tetraacetate
20.5% sodium sulfate
3.0% diperoxydicarboxylic acid
9.5% water.

A polyamide 6 textile is washed 5 times, at 55° C. with a liquor-to-goods ratio of 20:1, in a solution containing 4 g/l of the above washing composition and 0.09% by weight, based on the amount of washing composition of, as optical brightener, the compound of formula (103) of the application.

For the purpose of comparison, the test is repeated using, as optical brightener, compound 160 according to Sahm et al. U.S. Pat. No. 4,002,423, namely the compound having the formula:

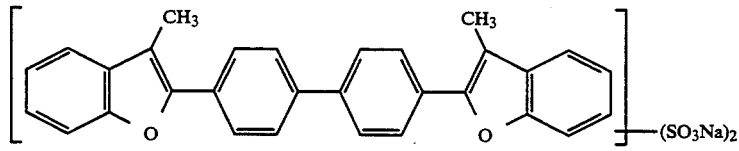

After washing, the textile is dried in the dark and then the degree of whiteness is determined, using a Zeiss RFC3-Photometer according to Ganz. The following results are obtained:

| optical brightener | whiteness |
| --- | --- |
| compound of formula (103) | 190 |
| Sahm compound 160 | 180 |

A difference in Ganz whiteness between 190 and 180 is substantial. This difference of 10 Ganz units is clearly perceivable by an untrained observer, and denotes that 30–50 at % more of an optical brightener with a Ganz whiteness of 180 will be needed relative to an optical brightener having a Ganz whiteness of 190.

EXAMPLE 18

A cotton textile is washed 5 times, at 60° C. with a liquor-to-goods ratio of 20:1, in a solution containing 4 g/l of the washing composition of Example 17, and a specified amount (see Table below), based on the weight of the washing composition, of an optical brightener of the application. After washing, the textile is dried in the dark, and then the degree of whiteness is determined using a Zeiss RFC3-Photometer according to Ganz.

For the purpose of comparison, the test is repeated using, as optical brightener, compound 102 of Sahm et al. U.S. Pat. No. 4,002,423, namely the compound having the formula:

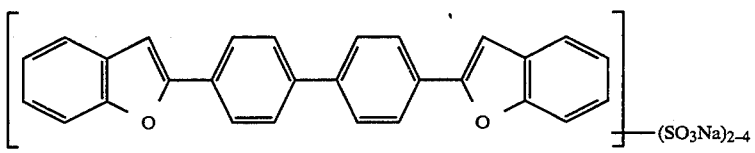

The following results are obtained.

| optical brightener | amount (%) | whiteness |
|---|---|---|
| compound of formula (103) | 0.10 | 190 |
| compound of formula (111) | 0.10 | 195 |
| Sahm compound 102 | 0.20 | 180 |

These results show the compounds of the instant application provide a better degree of whiteness than twice the amount of compound 102 according to Sahm.

EXAMPLE 19

A cotton textile is washed 5 times, at 60° C. with a liquor-to-goods ratio of 20:1, in a solution containing 4 g/l of the washing solution of Example 17, and a certain amount (see Table below), based on the weight of washing composition, of an optical brightener of the application. After washing, the textile is dried in the dark and then the degree of whiteness is determined using a Zeiss RFC3-Photometer according to Ganz. For the purpose of comparison, the test is repeated using, as optical brightener, compound A, namely the compound having the formula:

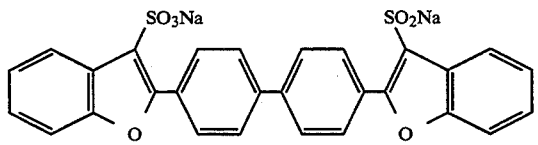

or compound (3), namely the compound having the formula:

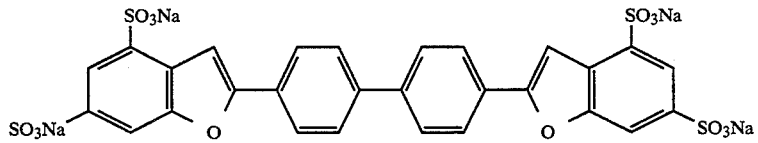

each according to Clements U.S. Pat. No. 5,089,166.
The following results are obtained.

| optical brightener | amount (%) | whiteness |
|---|---|---|
| compound of formula (103) | 0.10 | 190 |
| compound of formula (111) | 0.10 | 195 |
| Clements compound A | 0.15 | 190 |
| Clements compound (3) | 0.30 | 190 |

In order to achieve the degree of whiteness attained with compound (103) of the application, 50% more of Clements' compound A must be used, or 3 times as much of Clements' compound 3. Even using such excess amounts, the Clements' compounds do not reach the whiteness level of compound (111) of the application.

What is claimed is:

1. A dibenzofuranylbiphenyl compound of the formula (IV)

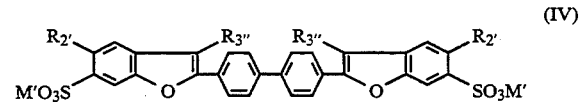

in which
$R_2'$ is hydrogen, methyl, ethyl, chlorine or methoxy and $R_3''$ is ethyl, chlorine or phenyl, or
$R_2'$ is methyl, ethyl, chlorine or methoxy and $R_3''$ is methyl, ethyl, chlorine or phenyl and
M' is hydrogen or one equivalent of a non-chromophoric cation.

2. A dibenzofuranylbiphenyl compound according to claim 1 wherein M' is hydrogen or sodium.

3. A dibenzofuranylbiphenyl compound according to claim 2 wherein $R_2'$ is hydrogen, methyl, ethyl, chlorine or methoxy and $R_3''$ is ethyl, chlorine or phenyl.

4. A dibenzofuranylbiphenyl compound according to claim 2 wherein $R_2'$ is methyl, ethyl, chlorine or methoxy and $R_3''$ is methyl, ethyl, chlorine or phenyl.

5. A dibenzofuranylbiphenyl compound according to claim 4 wherein $R_2'$ and $R_3''$ are each methyl.

6. A dibenzofuranylbiphenyl compound according to claim 5 wherein $R_2'$ is hydrogen and $R_3''$ is ethyl.

7. A dibenzofuranylbiphenyl compound according to claim 1 wherein $R_2'$ is hydrogen and $R_3''$ is chlorine.

8. A dibenzofuranylbiphenyl compound according to claim 3 wherein $R_2'$ is chlorine and $R_3''$ is ethyl.

* * * * *